(12) United States Patent
Liu

(10) Patent No.: US 10,414,821 B2
(45) Date of Patent: Sep. 17, 2019

(54) ANTI-PD-1 ANTIBODY AND USE THEREOF

(71) Applicant: LIVZON MABPHARM INC., Jinwan Zhuhai, Guangdong (CN)

(72) Inventor: Jie Liu, Jinan (CN)

(73) Assignee: LIVZON MABPHARM INC., Guangdong (CN)

( * ) Notice: Subject to any disclaimer, the term of this patent is extended or adjusted under 35 U.S.C. 154(b) by 101 days.

(21) Appl. No.: 15/328,462

(22) PCT Filed: Aug. 28, 2015

(86) PCT No.: PCT/CN2015/088384
§ 371 (c)(1),
(2) Date: Jan. 23, 2017

(87) PCT Pub. No.: WO2016/015685
PCT Pub. Date: Feb. 4, 2016

(65) Prior Publication Data
US 2017/0210806 A1    Jul. 27, 2017

(30) Foreign Application Priority Data

Jul. 30, 2014 (CN) .......................... 2014 1 0369300

(51) Int. Cl.
*C07K 16/18* (2006.01)
*A61K 39/395* (2006.01)
*C07K 16/28* (2006.01)
*A61K 39/00* (2006.01)
*A61P 35/00* (2006.01)

(52) U.S. Cl.
CPC .... *C07K 16/2818* (2013.01); *A61K 39/00115* (2018.08); *A61K 39/39558* (2013.01); *C07K 16/2809* (2013.01); *A61K 39/0011* (2013.01); *A61K 2039/505* (2013.01); *A61K 2039/507* (2013.01); *A61P 35/00* (2018.01); *C07K 2317/24* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search
CPC ................ C07K 16/2818; C07K 16/28; C07K 16/2803; A61K 31/39541; A61K 31/395; A61K 31/3955
See application file for complete search history.

(56) References Cited

PUBLICATIONS

Foote et al., J. Mol. Biol. 224 (1992): 487-499.*

* cited by examiner

*Primary Examiner* — Robert C Hayes
(74) *Attorney, Agent, or Firm* — Lewis Roca Rothgerber Christie LLP

(57) ABSTRACT

A PD-1 antibody or a functional fragment thereof, and use of said antibody in the preparation of a medicament for treating tumors are provided.

4 Claims, 5 Drawing Sheets
Specification includes a Sequence Listing.

ANTI-PD-1 ANTIBODY AND USE THEREOF

CROSS-REFERENCED TO RELATED APPLICATION(S)

This application is a US National Phase Patent Application of International Patent Application No. PCT/CN2015/088384, filed Aug. 28, 2015, which claims priority of Chinese Patent Application No. 201410369300.7, filed Jul. 30, 2014, the entire contents of all of which are hereby incorporated herein by reference.

INCORPORATION BY REFERENCE

The instant application contains a Sequence Listing which has been submitted in ASCII format via EFS-Web and is hereby incorporated by reference in its entirety. Said ASCII copy, was modified on Sep. 25, 2017, is named 134072SEQLIST.txt, and is 10,302 bytes in size.

TECHNICAL FIELD

The present invention provides a new anti-PD-1 antibody or a functional fragment thereof. In particular, the present invention further relates to use of the antibody in the preparation of a medicament for treating tumors.

BACKGROUND ART

T cell co-receptor signaling is an important mechanism for tightly regulating immune responses. The cell surface molecules for co-signaling (including co-stimulation and co-suppression) can be divided into two main families: immunoglobulin (Ig) superfamily and tumor necrosis factor (TNF)-tumor necrosis factor receptor (TNFR) superfamily. Generally, the activation of T cells is dependent on the antigen peptides presented by HLA class I or II molecules. Co-receptor signaling will either increase or prevent this activation. For example, the initiation and maturity of the lymphocytes in peripheral lymphoid organs can be promoted, or their response effects in an organism can be enhanced by such as the activation of CD28 or 4-1BB with agonists through the unique co-stimulation pathways. Immune activation could also be achieved by blocking co-suppression signaling pathways with antagonists, such as programmed cell death protein 1 (PD-1), B7 homolog 1 (B7-H1, also referred as PDL1) pathway, cytotoxic T lymphocyte antigen 4 (CTLA4), B/T lymphocyte attenuator (BTLA) and other pathways. These co-suppression signaling pathways play important roles in the regulation of immune tolerance, which provide negative signals that limit, terminate and/or attenuate immune responses. Immune activation mediated by co-stimulation receptors is activated by stimulating membrane-proximal kinase and produces phosphorylation cascade amplification, while co-suppression receptors such as CTLA4, PD1 and B/T lymphocyte attenuator (BTLA) recruit phosphatase to reverse the phosphorylation which is induced by immune activation. Immunomodulatory biological formulations can be widely used in the treatment of immune-related diseases, to inhibit the immune hyperfunction caused by transplant rejection, autoimmune disease or inflammatory disease, or to stimulate the immune response to immune hypofunction such as cancer, chronic bacterial infection and virus infection etc. Unlike the mainstream therapies based on monoclonal antibodies and recombinant fusion proteins, i.e. by neutralization or consumption of target antigens or target-positive cells, the immunomodulatory biological formulations regulate the signals for the antigen-specific T cell receptor (TCR) and B cell receptor(BCR) mainly by binding and regulating the signal molecules on the surface of the host's immune cells, so as to control the direction and intensity of the lymphocyte response.

PD-1 gene is up-regulated when T cell hybridoma undergoes apoptosis, and is named as programmed cell death protein 1. PD-1 (CD279) is expressed in activated T cells, B cells, and activated myeloid cells (Ishida Y, Agata Y, Shibahara K, Honjo T. EMBO J. 1992, 1: 3887-3895), and is also expressed in activated macrophages, DC and monocytes, but is not present in their immature cells (Agata Y, et al. Int. Immunol. 1996, 8: 765-772; Said E A, et al. Nature Med. 2010, 16: 452-459). These up-regulated expressions of PD-1 on cell surface can inhibit acquired immune and innate immune responses of an organism. PD-1 intracellular domain contains two tyrosine sites, one is immunoreceptor tyrosine-based inhibitory motif (ITIM), and the other is immunoreceptor tyrosine-based switch motif (ITSM). The phosphorylation of the tyrosine on ITSM recruits tyrosine phosphatase SHP2 and/or SHP1. These phosphatases will dephosphorylate ZAP70, CD3 and PKC, thereby attenuating T cell signals. PD-1 mainly inhibits T cell and B cell proliferation by causing the cells to be arrested in G0/G1 phase, and inhibits the cytokine production in T cells. The animals of PD-1 expression deletion develop various antoimmune phenotypes, including autoimmune cardiomyopathy, lupus-like syndromes with arthritis and nephritis (Nishimura et al. Immunity. 1999, H: 141-51; Nishimura et al. Science. 2001, 291: 319-22). In addition, PD-1 also plays an important role in autoimmune encephalomyelitis, systemic lupus erythematosus (SLE), graft-versus-host disease (GVHD), diabetes type I and rheumatoid arthritis, etc. (Salama et al. J Exp Med. 2003, 198: 71-78; Prokunina and Alarcon-Riquelme, Hum Mol Genet. 1992, 13: R143; Nielsen et al. Lupus. 2004, 11: 510).

Two PD-1 ligands have been currently reported, PD-L1/B7H1/CD274 and PD-L2/B7-DC/CD273 (Freeman G J, et al. J. Exp. Med. 2000, 192: 1027-1034; Latchman Y, et al. Nature Immunol. 2001, 2: 261-268). PD-L1 is expressed at a low level in immune cells, such as B cells, dendritic cells, macrophages and T cells, and is up-regulated upon cell activation. PD-L1 is also expressed in non-lymphoid organs such as vascular endothelial cells, heart, lung, pancreas, muscle, keratinocytes and placenta etc. The expression of PD-L1 in non-lymphoid tissue reveals that PD-L1 may regulate the function of self-reactive T cells, B cells and myeloid cells in peripheral tissues, and may also participate in inflammatory responses of a target organ. The expression of PD-L1 is mainly regulated by interferon 1 or 2, which are also the major regulators of PD-L1 level in vascular endothelial cells and epithelial cells. PD-L1 is also expressed in tumor cells, and is closely associated to poor prognosis. Various viral infections can induce the expression of PD-L1 in host tissues in a high level. Although PD-L2 transcript is found in non-hematopoietic tissues such as heart, liver and pancreas, the expression of PD-L2/B7-DC on cell surface is only restricted to macrophages and dendritic cells, and depends on the production of IFNγ and Th2 cytokines. The expressions of PD-L1 and PD-L2 are also affected by different stimulations. PD-L1 on macrophages is induced by INFy, while PD-L2 is regulated by IL-4. A similar phenomenon also appears on dendritic cells. The study reveals that PD-L1 might preferentially regulate Th1 response, while PD-L2 would regulate Th2 cell response. PD-L1 and PD-L2 both can inhibit T cell proliferation, cytokine production and the adhesion mediated by β1/β2 integrin. PD-L2 can also trigger the reverse signaling of dendritic cells, thereby resulting in IL-12 production and T cell activation.

PD-L1-PD-1 regulation axis plays a key role in the control of human T cell activation and the maintenance of organism immune tolerance, and is also utilized by tumor cell as well as virus in chronic virus infection (Yao S, Chen L. Trends Mol. Med. 2006, 12: 244-246; Zou W, Chen L. Nature Rev. Immunol. 2008, 8: 467-477). PD-L1 is highly expressed in a variety of human cancer tissues (Dong et al, Nat. Med. 2002, 8: 787-9). The expression of PD-L1 is associated to the progression and poor prognosis of certain types of malignancies (Thompson R H, et al. Cancer Res. 2006, 66: 3381-3385). PD-L1-PD1 pathway has also been confirmed to promote T cell depletion (Zajac A J, et al. J. Exp. Med. 1998, 188: 2205-2213). PD-L1-PD1 pathway caused by tumors or viruses can achieve the avoidance of host immunological surveillance through a variety of mechanisms, including promoting T cell inactivation, fatigue, unresponsiveness and apoptosis, inducing Treg cell amplification, and enhancing intrinsic ability of tumor to resist killing and apoptosis. The interaction of PD-1 and PD-L1 mediated by cancer cells results in the reduction of tumor infiltrating lymphocytes, the inhibition of T cell proliferation mediated by T cell receptors, and increased immune escape (Dong et al. J. Mol. Med. 2003, 81: 281-7; Blank et al. Cancer Immunol. Immunother. 2005, 54: 307-314; Konishi et al. Clin. Cancer Res. 2004, 10: 5094-100).

To date, there is still no a satisfactory method which can induce effective immune response for a cancer patient to specifically block PD-L1-PD-1 regulation axis, and to provide activation of anti-tumor and anti-virus immune response. Therefore, there is an urgent need for development and design of a therapeutic method to specifically block PD-L1-PD-1 regulation axis, to overcome the immunosuppression of the patients having a cancer or a chronic infection.

DISCLOSURE OF THE INVENTION

Generally, the present invention provides a new PD-1 antibody or a functional fragment thereof. In particular, the antibody of the present invention is a humanized antibody.

In one aspect, the present invention provides an antibody or a functional fragment thereof which can specifically bind to PD-1, wherein the antibody comprises a heavy chain and a light chain, wherein (i) the heavy chain comprises H-CDR1, H-CDR2 and H-CDR3, which have the amino sequences represented by SEQ ID NO: 7, 8 and 11, or 9, 10 and 11, respectively; and (ii) the light chain comprises L-CDR1, L-CDR2 and L-CDR3, which have the amino sequences represented by SEQ ID NO:12, 13 and 14, respectively.

In one aspect, the present invention provides an antibody or a functional fragment thereof which can specifically bind to PD-1, wherein (i) the heavy chain comprises a heavy chain variable region, which has the amino sequence represented by SEQ ID NO: 1, 2, 4 or 5; and (ii) the light chain comprises a light chain variable region, which has the amino sequence represented by SEQ ID NO: 3 or 6.

In another aspect, the present invention provides an antibody or a functional fragment thereof which can specifically bind to PD-1, wherein (i) the heavy chain comprises a heavy chain variable region, which has the amino sequence represented by SEQ ID NO: 4 or 5; and (ii) the light chain comprises a light chain variable region, which has the amino sequence represented by SEQ ID NO: 6.

Preferably, the anti-PD-1 antibody of the present invention is selected from 10F8, 15H6, BA08-1 and BA08-2.

In yet another aspect, the present invention provides an isolated polynucleotide, which encodes the anti-PD-1 antibody or a functional fragment thereof of the present invention.

In yet another aspect, the present invention provides a combination of isolated polynucleotides, which comprises a polynucleotide encoding the light chain of the anti-PD-1 antibody or a functional fragment thereof of the present invention, and a polynucleotide encoding the heavy chain of the anti-PD-1 antibody or a functional fragment thereof of the present invention.

In yet another aspect, the present invention provides an expression vector, which comprises the polynucleotide of the present invention or the combination of polynucleotides of the present invention, the polynucleotide effectively links to a regulatory sequence which allows the expression of a polypeptide encoded by the polynucleotide in a host cell or a cell-free expression system. Preferably, the expression vector is a viral vector or a non-viral vector.

In yet another aspect, the present invention provides a pharmaceutical composition, which comprises the anti-PD-1 antibody or a functional fragment thereof of the present invention, and a pharmaceutically acceptable carrier.

In yet another aspect, the present invention provides a method for treating or preventing a cancer or an infectious disease in a subject in need thereof, which comprises administering the anti-PD-1 antibody or a functional fragment thereof, the polynucleotide, the combination of polynucleotides, the expression vector and/or the pharmaceutical composition of the present invention to the subject. In some certain embodiments, the subject has received or intends to receive an anti-CD3 antibody therapy.

In yet another aspect, the present invention provides a method for enhancing T cell immune response in a subject in need thereof, which comprises administering the anti-PD-1 antibody or a functional fragment thereof, the polynucleotide, the combination of polynucleotides, the expression vector and/or the pharmaceutical composition of the present invention to the subject. In some embodiments, the enhancing T cell immune response includes enhancing cytokine production of T cells, preferably, the cytokine includes IL-2 and/or IFN-γ. In some preferred embodiments, the enhancing cytokine production of T cells includes the cytokine production of T cells stimulated by an anti-CD3 antibody. In some other preferred embodiments, the subject is a patient with a cancer, for example, a patient with PD-L1 positive cancer, preferably a patient with lung cancer and melanoma.

In yet another aspect, the present invention provides a method for promoting T cell activation in a subject in need thereof, which comprises administering the anti-PD-1 antibody or a functional fragment thereof, the polynucleotide, the combination of polynucleotides, the expression vector and/or the pharmaceutical composition of the present invention to the subject. Preferably, the method further comprises administering an anti-CD3 antibody to the subject.

In yet another aspect, the present invention provides a method for eliminating the inhibition of PD-L1 on T cell activation in a subject in need thereof, which comprises administering the anti-PD-1 antibody or a functional fragment thereof, the polynucleotide, the combination of polynucleotides, the expression vector and/or the pharmaceutical composition of the present invention to the subject. Preferably, the method further comprises administering an anti-CD3 antibody to the subject.

In yet another aspect, the present invention provides a method (preferably in vitro) for promoting T cell activation, which comprises contacting the anti-PD-1 antibody or a functional fragment thereof, the polynucleotide, the combination of polynucleotides, the expression vector and/or the pharmaceutical composition of the present invention with T cells. Preferably, the method further comprises contacting an anti-CD3 antibody with T cells.

In yet another aspect, the present invention provides a method (preferably in vitro) for eliminating the inhibition of PD-L1 on T cell activation, which comprises contacting the anti-PD-1 antibody or a functional fragment thereof, the polynucleotide, the combination of polynucleotides, the expression vector and/or the pharmaceutical composition of the present invention with T cells. Preferably, the method further comprises contacting an anti-CD3 antibody with T cells.

In yet another aspect, the method of the invention further provides a combination therapy, which comprises administering the anti-PD-1 antibody Of the present invention and an anti-CD3 antibody to a subject in need thereof.

In yet another aspect, the present invention provides use of the anti-PD-1 antibody or a functional fragment thereof of the present invention in the preparation of a medicament for treating or preventing a cancer or an infectious disease.

In yet another aspect, the present invention provides use of the anti-PD-1 antibody or a functional fragment thereof of the present invention in the preparation of a medicament for enhancing T cell immune response. In some embodiments, the enhancing T cell immune response includes enhancing cytokine production of T cells, preferably, the cytokine includes IL-2 and/or IFN-γ. In some preferred embodiments, the enhancing cytokine production of T cells includes the cytokine production of T cells stimulated by an anti-CD3 antibody.

In some embodiments, the anti-PD-1 antibody or a functional fragment thereof of the present invention can be used for treating PD-L1 positive cancer and PD-1 negative cancer. In some certain embodiments, the cancer is lung cancer or melanoma (for example, PD-L1 positive lung cancer or melanoma and/or PD-L1 negative lung cancer or melanoma), and the infectious disease is a HIV infection or a hepatitis B virus infection.

In some certain embodiments, the anti-PD-1 antibody or a functional fragment thereof according to the present invention blocks the interaction between PD-1 and PD-L1 and/or the interaction between PD-1 and PD-L2.

In some preferred embodiments, the anti-PD-1 antibody or a functional fragment thereof of the present invention further comprises a human IgG4 or IgG1 heavy chain constant region and a human κ light chain constant region.

The present invention also relates to a method for screening and preparing the humanized antibody described above: immunizing BLAC/C mice with human PD-1 protein, screening the mouse antigen-specific B cells of a high titer through a flow cytometer, cloning the genes of the antibody heavy chain and light chain variable region with a RT-PCR method, then expressing the recombinant antibody using 293 cells. After purifying with protein A, and through screening for affinity and blocking the binding activity with PD-L1, antibodies 10F8 and 15H6 are finally selected with the unexpected high PD-1 affinity and T cell activation ability. The amino acid sequences of the heavy chain variable region of antibodies 10F8 and 15H6 are represented by SEQ ID NO: 1 and 2, respectively; the two antibodies contain the light chain variable region with the same amino acid sequence, as represented by SEQ ID NO: 3. The amino acid sequences of heavy chain CDRs (H-CDR1, H-CDR2 and H-CDR3) of antibody 10F8 are represented by SEQ ID NO: 7, 8 and 11, respectively; the amino acid sequences of the heavy chain CDRs (H-CDR1, H-CDR2 and H-CDR3) of 15H6 are represented by SEQ ID NO: 9, 10 and 11, respectively; the amino acid sequences of the light chain CDRs (L-CDR1, L-CDR2 and L-CDR3) of antibodies 10F8 and 15H6 are represented by SEQ ID NO: 12, 13 and 14, respectively. Based on their heavy chain variable region FR1, FR2, FR3 and FR4 sequences, a comparison is made against the human antibody gene sequence library, and a series of the corresponding candidate sequences of the variable regions of a human germ line antibody are found, which are similar with the heavy chain variable region FR1, FR2, FR3 and FR4 sequences. The binding affinities of the series of candidate sequences with HLA-DR molecules are analyzed by a computer simulation (in silicon) method, to select the frame sequences of the lowest affinity, thereby to finally establish the humanized sequences of FR1, FR2, FR3 and FR4 of the heavy chain variable region. On the basis of those frame sequences, computer molecular model analysis is applied to analyze the corresponding frame amino residues reserved in the murine antibody required to support CDR configuration. The amino acid sequences of the heavy chain variable region of humanized antibody BA08-1 corresponding to 10F8 and humanized antibody BA08-2 corresponding to 15H6 are represented by SEQ ID NO: 4 and 5, respectively. The same analysis is carried out on the sequence of the light chain variable region of the mouse antibody. Based on the sequences of the light chain variable region FR1, FR2, FR3 and FR4, a comparison is made against the human antibody gene sequence library (NCBI lg BLAST), and the corresponding candidate sequences of the variable regions of a human germline antibody are found, which are similar with the light chain variable region FR1, FR2, FR3 and FR4 sequences. The binding affinities of the sequences with HLA-DR molecules are analyzed by computer (in silicon) analysis, and the frame sequences with the lowest affinity are selected, thereby to finally establish the humanized sequences of FR1, FR2, FR3 and FR4 of the light chain variable regions. On the basis of those frame sequences, computer molecular model analysis is applied to analyze the spatial stereo structure of the mouse antibody, and to analyze the corresponding frame amino residues reserved in the murine antibody light chain required to support CDR configuration. The light chain variable regions of humanized antibody BA08-1 and humanized antibody BA08-2 corresponding to 10F8 and 15H6 are represented by SEQ ID NO: 6.

SPECIFIC EMBODIMENTS

Figure 1:
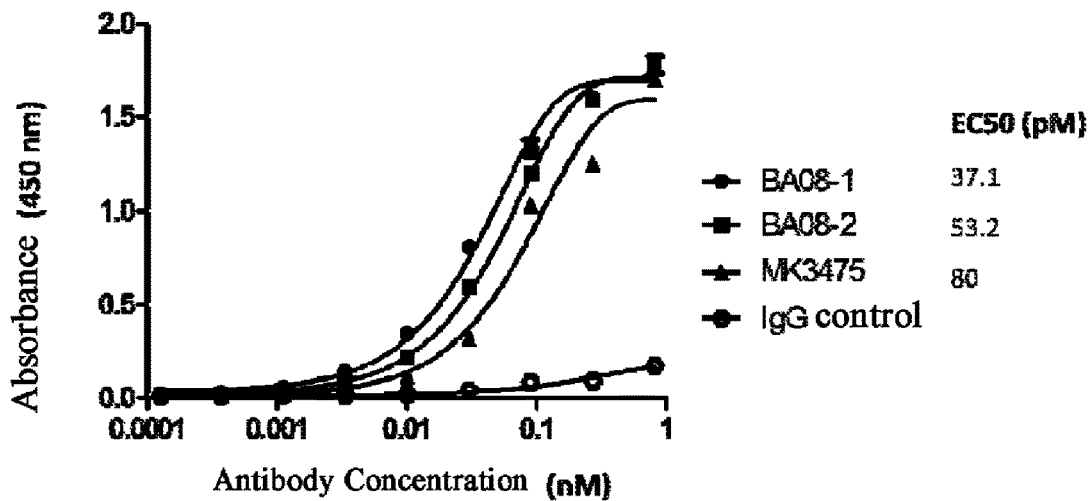
FIG. 1 shows that antibodies BA08-1 and BA-08-2 bind to PD-1 protein with high affinity.

Unless otherwise defined, all technical and scientific terms used herein have the same meanings as understood by those of ordinary skill in the art. For definitions and terminology in the art, specific reference can be made to Current Protocols in Molecular Biology (Ausubel) by professionals. The abbreviations for amino acid residues are the standard 3-letter and/or 1-letter codes for any one of the 20 L-amino acids commonly used in the art.

The present invention provides an anti-PD-1 antibody and a functional fragment thereof which can bind to programmed death factor 1 (PD-1). The antibody or a functional fragment thereof of the present invention has at least one of the following characteristics: being able to block the interaction of PD-1 and PD-L1 with high affinity; being able to bind to PD-1 with high specificity; activating tumor-specific T cells, thereby killing tumor cells; significantly enhancing T cell immune response, e.g., enhancing cytokine (including IFNγ and IL-2) production of T cells; and greatly increasing levels of immune effectors.

The present invention also provides a humanized anti-PD-1 antibody and a functional fragment thereof. For example, the humanized antibody is obtained by computer simulation design of the mouse-derived antibody produced by an immunized mouse in combination with yeast display technology.

On the premise of not substantially influencing the activity of the antibody, substitution, addition and/or deletion of one or more (such as 1, 2, 3, 4, 5, 6, 7, 8, 9 or 10 or more) amino acids in the sequences of the present invention can be made by those skilled in the art in order to obtain the variants of the sequence of the antibody or a functional fragment thereof. They are considered to be included within the protection scope of the present invention. For example, an amino acid in the variable regions can be replaced with that of similar property. The sequence of the variant of the invention may have at least 95%, 96%, 97%, 98% or 99% identity to the source sequence. The sequence identity of the present invention can be measured by sequence analysis software. For example, computer program BLAST with default parameters, especially BLASTP or TBLASTN can be used.

As used herein, the term "antibody" encompasses full-length antibodies (e.g., IgGI or IgG4 antibody), various functional fragments thereof (e.g. which may only comprise an antigen-binding portion, such as Fab, F (ab')$_2$ or scFv fragment), and modified antibodies (e.g., humanized, glycosylated, etc.). The present invention comprises the anti-PD-1 antibody with a modified glycosylation pattern. In some applications, the modification of removing the undesired glycosylation sites may be useful, or the absence of fucose moiety on the oligosaccharide chain of the antibody, for example, enhances the antibody dependent cellular cytotoxicity (ADCC) function. In other applications, a galactosylation modification can be conducted to change the complement-dependent cytotoxicity (CDC).

As used herein, the term "functional fragment" is intended to represent a fragment that reserves the function of a full-length antibody, e.g., an antigen-binding fragment, particularly the following antibody fragments: e.g. Fv, scFv (sc refers to a single strand), Fab, F (ab')$_2$, Fab', scFv-Fc fragment or diabody, or any fragments which are chemically modified or incorporated into a liposome to extend the half-life, and the chemical modification is for example the addition of poly(alkylene)glycol, such as polyethylene glycol ("pegylation, PEG-based") (the pegylated fragments are referred to as Fv-PEG, scFv-PEG, Fab-PEG, F(ab')$_2$-PEG or Fab'-PEG) ("PEG" is polyethylene glycol).

The DNA molecule encoding the anti-PD-1 antibody of the present invention can be cloned into a vector by those skilled in the art, and then transformed into host cells. Accordingly, the present invention also provides a recombinant DNA vector, which comprises a DNA molecule encoding the anti-PD-1 antibody of the present invention.

Preferably, the recombinant DNA vector is an expression vector, and those skilled in the art can clone the DNA molecule of the antibody into the expression vector and transform it into host cells to obtain the antibody by means of induction expression. The expression vector of the present invention contains the DNA sequences encoding the heavy chain variable region, the light chain variable region and/or the constant region of the anti-PD-1 antibody. However, the two expression vectors can be constructed separately, with one containing the heavy chain variable region and the constant region, and another containing the light chain variable region and the constant region, which transfect a mammal together. In one preferred embodiment, the expression vector further comprises a promoter and a DNA sequence encoding a secretion signal peptide, and at least one drug-resistance gene for screening.

The host cell of the present invention may be a prokaryotic host cell, an eukaryotic host cell or a bacteriophage. The prokaryotic host cell may be *Escherichia coli, Bacillus subtilis, Streptomyces* or *Proteus mirabilisetc*. The eukaryotic host cell may be fungi such as *Pichia pastoris, Saccharomyces cerevisiae, Schizosaccharomycespombe, trichoderma* etc.; insect cell such as *Mythimnaseparate*; plant cell such as tobacco, and mammalian cell such as BHK cell, CHO cell, COS cell, myeloma cell etc. In some embodiments, the host cell of the present invention is preferably mammalian cell, more preferably BHK cell, CHO cell, COS cell, NSO cell or COS cell.

As used herein, the term "pharmaceutical composition" refers to a combination of at least one drug and optionally a pharmaceutically acceptable carrier or excipient, which are combined together to achieve a special purpose. In certain embodiments, the pharmaceutical composition comprises a combination of the components separated in terms of time and/or space, as long as they can function collectively to realize the purpose of the present invention. For example, the ingredients contained in the pharmaceutical composition (e.g., the antibody, the nucleic acid molecule, the combination of nucleic acid molecules and/or the conjugate according to the present invention) may be administered to a subject as a whole, or administered to a subject separately. When the ingredients contained in the pharmaceutical composition are administered to the subject separately, said ingredients can be administered to the subject simultaneously or sequentially. Preferably, the pharmaceutically acceptable carrier is water, a buffer solution, an isotonic salt solution such as PBS (phosphate buffered saline), glucose, mannitol, dextrose, lactose, starch, magnesium stearate, cellulose, magnesium carbonate, 0.3% glycerol, hyaluronic acid, ethanol, or polyalkylene glycols such as polypropylene glycol, triglyceride, and the like. The type of the pharmaceutically acceptable carrier depends on the particular route of administration for which the composition of the invention is formulated, such as oral, nasal, intradermal, subcutaneous, intramuscular or intravenous administration. The composition of the invention may contain wetting agents, emulsifying agents or buffer substances as additives.

The pharmaceutical compositions according to the present invention may be administered via any suitable route, for example oral, nasal, intradermal, subcutaneous, intramuscular, or intravenous administration.

In a related aspect, the present invention provides a pharmaceutical composition which is a combination of the anti-PD-1 antibody with a second therapeutic agent. In one embodiment, the second therapeutic agent is any agent advantageously combined with the anti-PD-1 antibody. The exemplary agent which is advantageously combined with the anti-PD-1 antibody include, but are not limited to, other agents inhibiting PD-1 activity (including other antibodies or the antigen binding fragments thereof, peptide inhibitors, small molecule antagonists, etc.) and/or agents interfering upstream or downstream signal transduction of PD-1. Preferably, the second therapeutic agent is an anti-CD3 antibody.

As used herein, the term "PD-L1 positive cancer or infectious disease" is intended to refer to the cancer or infectious disease which is resulted from PD-1 expression or has the symptom/characteristic of PD-1 expression. The cancer includes, but are not limited to lung cancer, liver cancer, ovarian cancer, cervical cancer, skin cancer, bladder cancer, colon cancer, breast cancer, glioma, renal cancer, gastric cancer, esophageal cancer, oral squamous cell carcinoma, head and neck cancer. The infectious disease includes, but are not limited to HIV virus infection and Hepatitis B virus infection.

"Therapeutically effective amount" as used herein refers to a dosage sufficient to confer benefit to a subject to which it is administered. The actual amount administered, and the rate and time-course of administration will depend on the condition and the severity of the subject being treated. The prescription of treatment (e.g., dose determination) is ultimately the responsibility of a general practitioner and other doctors, and will depend on their decisions, generally considering the disease being treated, the condition of individual patient, the site of delivery, the method of administration and other factors known for doctors.

The term "subject" as used herein refers to a mammal, such as a human, but may also be other animals, such as wild animals (such as heron, stork, crane, etc.), livestock (such as duck, goose, etc.) or laboratory animals (such as orangutan, monkey, rat, mouse, rabbit, guinea pig, etc.).

The following examples are provided to demonstrate and further explain some preferred embodiments and aspects of the present invention, and should not be construed as limiting the scope thereof.

EXAMPLES

Example 1. Production of Mouse Anti-PD-1 Monoclonal Antibody 6-10 weeks old BALB/C mice were subcutaneously (SC) immunized by recombinant fusion protein PD-1-mFc antigen comprising PD-1 extracellular portion (25 µg) (Sino Biological Inc, Cat lot: 10377-H08H). The mice were initially immunized by inoculation of the antigen mixed with Freund's complete adjuvant (F5881, Sigma), followed by a subcutaneous immunization inoculation of the antigen mixed with Freund's incomplete adjuvant antigen (F5506, Sigma) (total of 6 immunizations, at day 1, 7, 14, 28, 60 and 64, respectively). The immune response was monitored by blood sampling from the orbital venous plexus. The antiserum was screened by ELISA, and the purified recombinant PD-1 fusion protein (Sino Biological Inc, Cat lot: 10377-H08H) was diluted to 1 µg/ml with PBS, coated into a microwell plate with 100 µl/well, and incubated at 4° C. overnight. The wells then were blocked with a PBS solution containing 5% fetal bovine serum and 0.05% Tween 20 at 200 µl/well. After a gradient dilution, the serum of PD-1 immunized mice was added to each well and incubated at room temperature for 1 hour. After washing the plate with a PBS/Tween-20 solution, horseradish peroxidase-coupled goat anti-mouse IgG polyclonal antibody (Jackson Immunoresearch Labs, Cat #: 115-035-044) was added and incubated for 1 hour at room temperature. After washing the plate, the plate was visualized with TMB substrate (Pierce, Cat #34021), and detected under OD 450. According to titer comparison, the mice with a high titer of anti-PD-1 immunoglobulin were used for isolation of the PD-1-specific B cells. The B lineage cells of each mouse were separated by fluorescence-activated cell sorting (FACS) according to the binding with biotin-labeled PD-1, and the gene transcripts of the corresponding full-length Ig heavy chain (H) variable region and Ig light (L) chain variable region were amplified by RT-PCR. According to the manufacturer's protocol, the amplified products were cloned into a 293 expression system (Life Technology). A protein A column was used to purify the resulting monoclonal antibody, which was further analyzed for the ability of binding with PD-1 and blocking the interaction between PD-1 and PD-L1. According to the ability of the antibody to block the binding of PD-1 with PD-L1, 10F8 and 15H6 were selected as the candidate clones for further research and development of the humanized antibodies.

Example 2. Design of Heavy Chain Variable Region Sequence of Humanized Monoclonal Anti-PD-1 Receptor Antibody The amino acid sequences encoding the heavy chain variable region of 10F8 and 15H6 monoclonal antibodies are represented by SEQ ID NO: 1 and SEQ ID NO: 2, respectively. The human germ line frame sequences with low immunogenicity were chosen by a comparison to the known sequence of human germline immunoglobulin heavy chain, and it was finally determined that human germline VH 3-66 segment, undetermined D segment and human germ line JH4 segment could be used as humanized 10F8 and 15H6 heavy chains. The amino acid sequences of humanized 10F8 (i.e. BA08-1) and humanized 15H6 (i.e. BA08-2) heavy chain variable regions were SEQ ID NO: 4 and SEQ ID NO: 5, respectively.

TABLE 1

The heavy chain CDRs (H-CDRs) of the antibody of the present invention

|  | 10F8 | 15H6 |
| --- | --- | --- |
| H-CDR1 | SEQ ID No: 7 | SEQ ID No: 9 |
| H-CDR2 | SEQ ID No: 8 | SEQ ID No: 10 |
| H-CDR3 | SEQ ID No: 11 | SEQ ID No: 11 |

Example 3. Design of Light Chain Variable Region Sequence of Humanized Monoclonal Anti-PD-1 Receptor Antibody The amino acid sequences of 10F8 and 15H6 light chain variable regions are identical (SEQ ID NO: 3). A human germline frame sequence with low immunogenicity was chosen by a comparison with the known sequence of the human germline immunoglobulin heavy chain, and it was finally determined that human germ line VH 3-11 segment and JK4 segment could be used as humanized 10F8 and 15H6 light chains. The amino acid sequence of the light chain variable region shared by humanized 10F8 (BA08-1) and humanized 15H6 (BA08-2) is SEQ ID NO: 6.

TABLE 2

The light chain CDRs (L-CDRs) of the antibody of the present invention

|  | 10F8 | 15H6 |
| --- | --- | --- |
| L-CDR1 | SEQ ID No: 12 | SEQ ID No: 12 |
| L-CDR2 | SEQ ID No: 13 | SEQ ID No: 13 |
| L-CDR3 | SEQ ID No: 14 | SEQ ID No: 14 |

Example 4. Expression and Preparation of Humanized Anti-PD-1 Receptor Monoclonal Antibody IgG4 Fc fragment sequence of human IgG4 heavy chain constant region (J Ellison, J Buxbaum, L Hood-DNA, 1981) and K fragment sequence of the light chain constant region (Hieter, P. A., Max, E. E., Seidman, J. G., Maizel, J. V. Jr., and Leder, P. Cell. 1980; 22: 197-207) were both synthesized by IDT Inc. (Integrated DNA Technologies, Coralville, Iowa). Vectors pBA-H4 and pBA-Ck of the present invention were constructed with pcDNA3 as backbones, wherein pBA-H4 (containing the human IgG4 heavy chain constant region IgG4Fc), and pBA-Ck (containing the human light chain constant region κ fragment) vectors were constructed by Bioabs Inc. In pBA-H4, a CMV promoter is used for the VH and CH, and a PGK promoter is used for puromycin resistance gene, while in pBA-Ck, a CMV promoter is used for the VL and a SV40 promoter is used for neomycin resistance gene. In accordance with the protein sequences of the heavy chain variable region sequence and light chain variable region of the antibody, the DNA sequences encoding the heavy chain variable regions and light chain variable regions were designed, which were further optimized for the optimized expression in CHO cells, wherein the DNA sequences encoding the heavy chain variable region of the humanized anti-PD-1 antibody of the present invention are represented by SEQ ID NO: 15 (BA08-1) and 16 (BA08-2), respectively, and the DNA sequence encoding the light chain variable region of the humanized anti-PD-1 antibody of the present invention is represented by SEQ ID NO: 17. The DNAs encoding the optimized heavy chain variable region and light chain variable region were synthesized by IDT Inc. (Integrated DNA Technologies, Coralville, Iowa). By using In-Fusion® HD clone kit (Clontech Cat #: 638910), the synthesized DNA fragment containing the heavy chains of BA08-1 and BA08-2 was directly cloned into pBA-H4 vector linearized with Nhe I enzyme, and the synthesized DNA fragment containing the light chains of BA08-1 BA08-2 was directly cloned into pBA-Ck vector linearized with BsiWI enzyme, followed by transformation into DH5α bacteria, and extraction of the plasmids and sequencing, and the sequencing result is consistent with the DNA coding sequences of the designed humanized antibody. CHO-S cells (available from Invitrogen) were cultured with 1×CD-CHO (available from GIBCO), 1×HT (available from GIBCO), 8 mM glutamine (available from GIBCO), in an incubator at 37° C., 8% $CO_2$. The CHO-S cells were co-transfected with the plasmids containing the heavy chain and light chain of antibodies BA08-1 and BA08-2, and the transfection method is in accordance with the instructions for DMRIE-C transfection kit (purchased from Invitrogen). 3 days after the transfection, the cells were cultured in the above described culture medium and 500 μg/ml G418 (available from GIBCO) and 12.5 μg/ml puromycin (available from Sigma) were added for pressurized screening. 14 days after pressurizing, the positive clones were selected, cultured in a six-well plate and detected by a direct ELISA method for the expression quantity of the antibody. The positive clone with the highest expression rate was selected, cultured in a large scale for 10 days, and then centrifuged to collect the culture supernatant, which was purified by a protein A affinity chromatography column (available from GE), dialyzed into PBS, and filtered through a 0.22 μm membrane for the various studies.

Example 5. Binding Specificity and Relative Affinity Between Antibody and PD-1

The relative binding of the antibody of the present invention with human PD-1 was determined by a protein-based ELISA method. Briefly, the purified recombinant PD-1 fusion protein (Sino Biological Inc, Cat #: 10377-H08H) was diluted to 1 μg/ml with BPS, coated onto a microwell plate with 100 μl/well, and incubated at 4° C. overnight. The wells then were blocked with a PBS solution containing 5% fetal bovine serum and 0.05% Tween 20 at 200 μl/well. After a gradient dilution, the anti-PD-1 antibody of the present invention, MK3475 (a MK-3475 analog control constructed by the present inventor using an expression vector of the present invention according to the disclosed MK3475 sequence, hereinafter referred to as MK3475 for short, the specific construction protocol is similar with the present invention) and IgG control were added to each well and incubated at room temperature for 1 hour. After washing the plate with a PBS/Tween-20 solution, horseradish peroxidase-coupled goat anti-human IgG polyclonal antibody (Jackson Immunoresearch Labs, Cat #:109-035-088) was added and incubated for 1 hour at room temperature. After washing the plate, the plate was visualized with TMB substrate (Cat #34021, Pierce), and detected under OD 450. The ELISA result is shown in FIG. 1. The affinity measured by Blitz instrument (Pall life Science) is shown in Table 3.

The antibody of the present invention exhibits the unexpected high binding affinity and binding specificity with PD-1.

TABLE 3

Binding kinetics of anti-PD-1 antibody

| Antibody | ka | kd | KD |
| --- | --- | --- | --- |
| BA08-1 | 1.22E+6 | 3.9E−6 | 4.8E−12 |
| BA08-2 | 1.15E+6 | 7.91E−6 | 9.1E−12 |

Example 6. Anti-PD-1 Antibody Blocks Binding of PD-L1 Ligand with PD-1 Receptor

Figure 2:
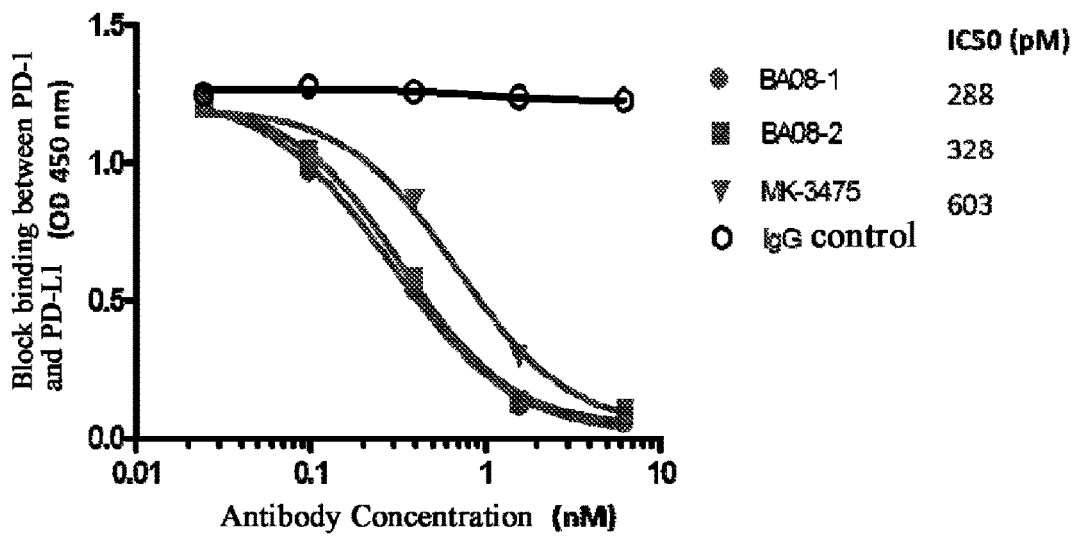
FIG. 2 shows that antibodies BA08-1 and BA-08-2 block the binding of PD-L1 and PD-1.

The humanized anti-PD-1 antibody of the present invention was tested for the manner of blocking the binding of PD-1 with its ligand. Specifically, a 96-well plate was coated by 1 μg/ml unlabeled hPD-L1/Fc (R&D Systems, Cat #156-B7-100) for 16 hours. 0.5 μg/ml PD-1 protein was pre-incubated with the recombinant anti-PD-1 antibodies of the different concentrations at 37° C. for 30 minutes, then added into a microwell plate for reaction. The PD-1 protein binding to the coated PD-L1 was hybridized with a mouse anti-human PD-1 antibody (eBioscience, Cat #14-9989-8214), and further detected with a method based on a horseradish peroxidase-coupled goat anti-mouse antibody. After washing the plate, the plate was visualized with TMB substrate (Pierce, Cat #34021), and detected under OD 450. As shown in FIG. 2, anti-PD-1 BA08-1 and BA08-2 antibodies specifically blocked the binding of PD-1 with its ligand PD-L1 (FIG. 2), with the blocking effect significantly better than that of MK-3475. Thus, the antibody of the present invention achieves the surprisingly higher blocking against the binding of PD-L1 and PD-1.

Figure 3:
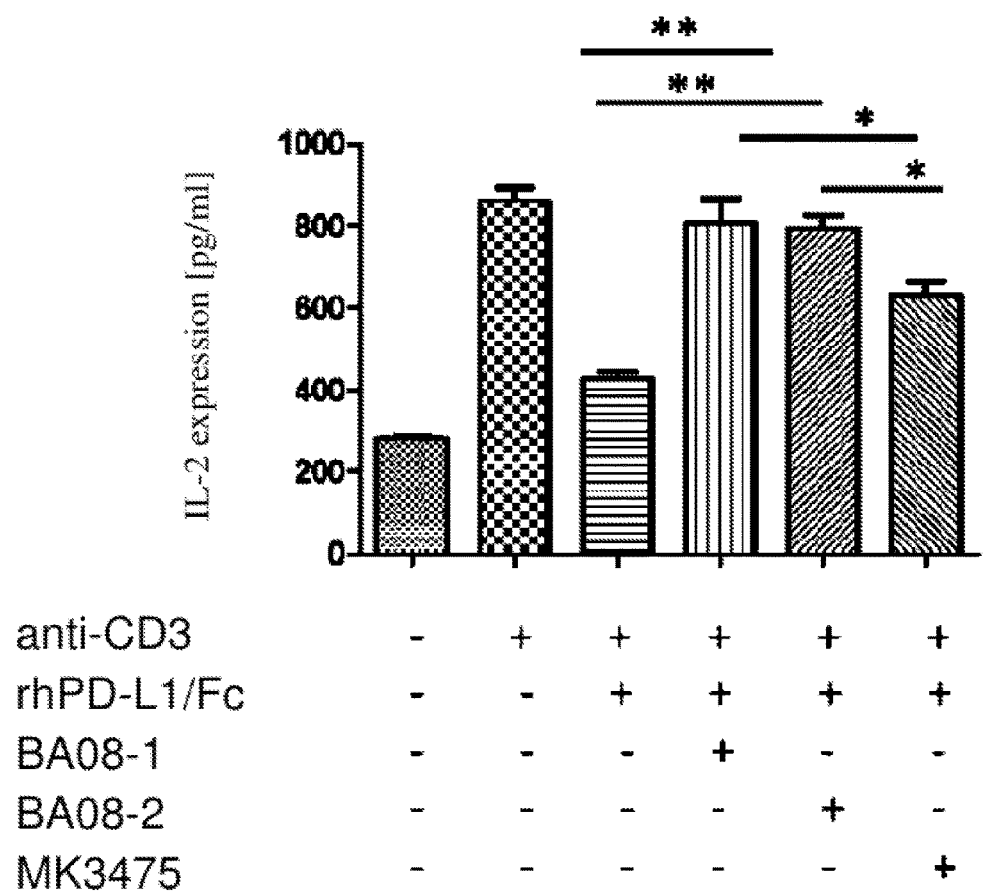
FIG. 3 shows that antibodies BA08-1 and BA-08-2 significantly enhance IL-2 production of T cells. The columns show from left to right: negative control without the antibody, positive control (anti-CD3 antibody alone), inhibition of PD-L1 on anti-CD3 antibody stimulated IL-2 expression (with the addition of PD-L1 and anti-CD3 antibody), antagonism of PD-L1 inhibitory effect by antibody BA08-1 of the present invention (with the addition of BA08-1, PD-L1 and anti-CD3 antibody), antagonism of PD-L1 inhibitory effect by antibody BA08-2 of the present invention (with the addition of BA08-2, PD-L1 and anti-CD3 antibody), and antagonism of PD-L1 inhibitory effect by MK3475 (with the addition of MK3475, PD-L1 and anti-CD3 antibody), as specified in the legends in the lower part of the figure.
Figure 4:
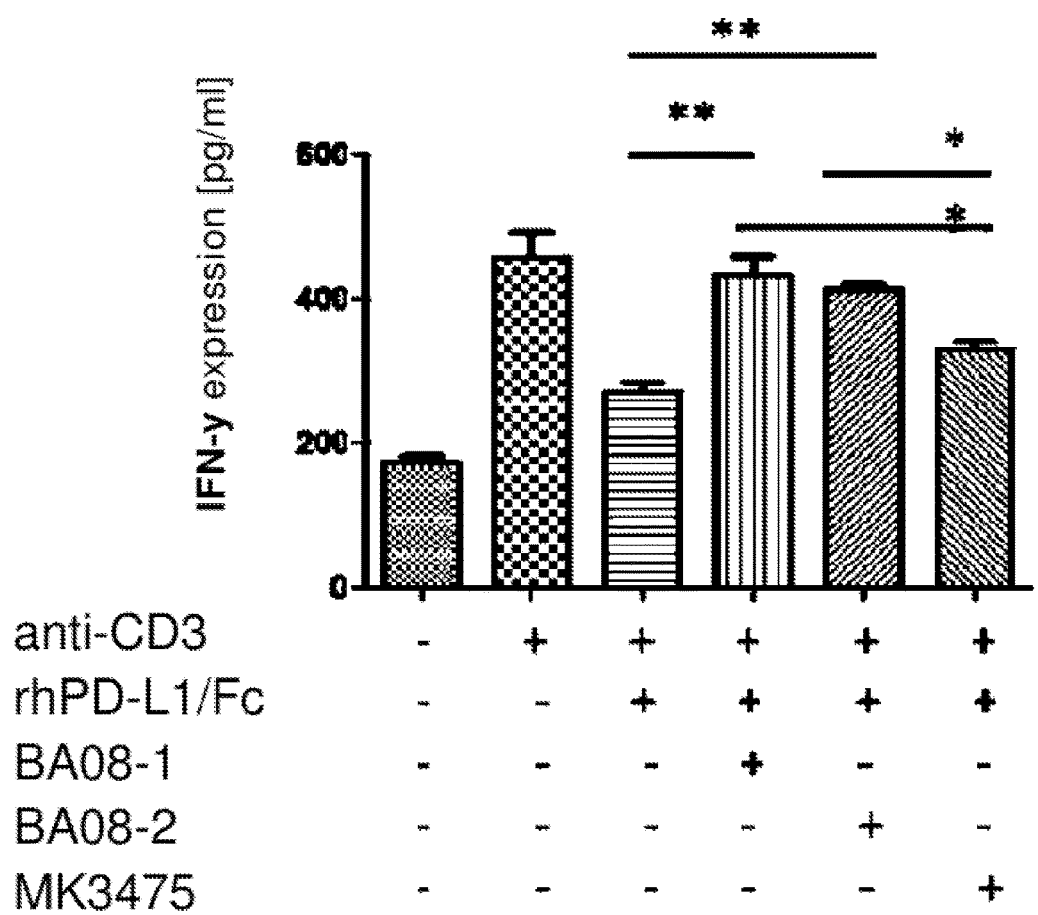
FIG. 4 shows that antibodies BA08-1 and BA-08-2 significantly enhance IFN-γ production of T cells. The columns show from left to right: control without CD3 antibody, positive control (anti-CD3 antibody alone), inhibition of PD-L1 on anti-CD3 antibody stimulated IFN-γ expression (with the addition of PD-L1 and anti-CD3 antibody), antagonism of PD-L1 inhibitory effect by antibody BA08-1 of the present invention (with the addition of BA08-1, PD-L1 and anti-CD3 antibody), antagonism of PD-L1 inhibitory effect by antibody BA08-2 of the present invention (with the addition of BA08-2, PD-L1 and anti-CD3 antibody), and antagonism of PD-L1 inhibitory effect by MK3475 (with the addition of MK3475, PD-L1 and anti-CD3 antibody), as specified in the legends in the lower part of the figure.

Example 7. Effect of Anti-PD-1 Antibody on Inhibition by Mediated PD-L1 Against Human T Cell Activity Human peripheral blood mononuclear cells (PBMC) were isolated from healthy donors by Ficoll method. Peripheral blood T cells of resting human were obtained by a negative selection through CD3+ T cell enriching column (R&D Systems). A 96-well plate was coated by 500 ng/mL anti-CD3 antibody and 1 μg/ml recombinant human PD-L1/Fc overnight at 4° C. 1 μg the anti-PD-1 antibody of the present invention or MK3475 was added to each well, and incubated at 37° C. for 4 hours. A RMPI suspension of isolated T cells ($2\times10^4$) was added, and the supernatant was collected after culturing for 2 days. IL-2 and IFN-γ expressions were detected with IL-2 ELISA kit (eBioscience Cat #88-7025-88) and IFN-γ ELISA kit (R&D Systems) respectively according to the instructions for use. As shown in FIG. 3 and FIG. 4, the columns show from left to right: control without CD3 antibody, positive control (anti-CD3 antibody was used alone), inhibition of PD-L1 on the IL-2 or IFN-γ expression stimulated by anti-CD3 antibody (with the addition of PD-L1 and anti-CD3 antibody), antagonism of antibody BA08-1 of the present invention to PD-L1 inhibitory effect (with the addition of BA08-1, PD-L1 and anti-CD3 antibody), antagonism of antibody BA08-2 of the present invention to PD-L1 inhibitory effect (with the addition of BA08-2, PD-L1 and anti-CD3 antibody), and antagonism of MK3475 to PD-L1 inhibitory effect (with the addition of MK3475, PD-L1 and anti-CD3 antibody). Anti-PD-1 BA08-1 and BA08-2 antibodies both significantly eliminate the inhibitory effect of PD-L1 on the IL-2 and IFN-γ production of CD3-stimulated T cells (**$p<0.01$), with the immune-enhancing effect which is significantly higher than that of MK-3475 analog (*$p<0.05$).

Figure 5:
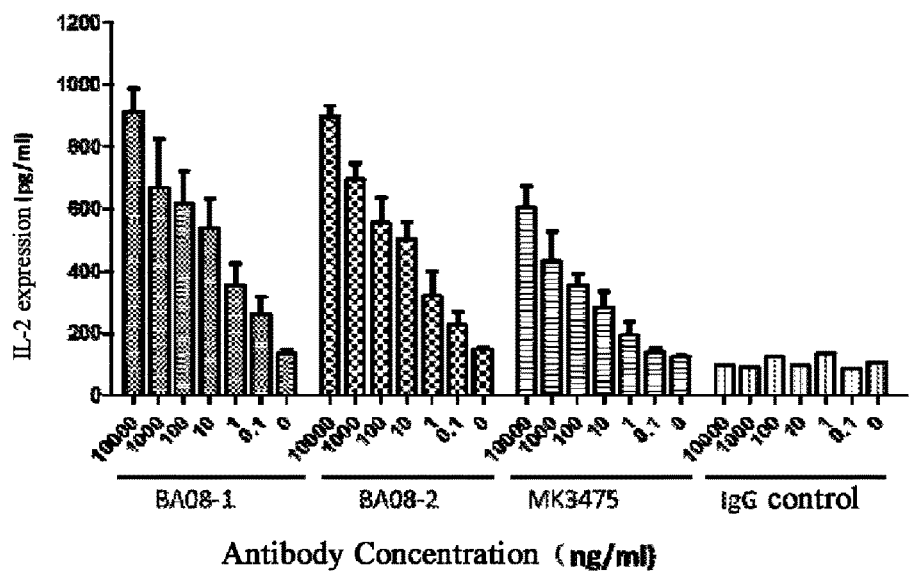
FIG. 5 shows the effects of antibodies BA08-1 and BA-08-2 on the cytokine production of lymphocytes.

Example 8. Effect of Anti-PD-1 Antibody on Cytokine Expression in Mixed Lymphocyte Reaction The effect of blocking PD-L1/PD-1 pathway on effector lymphocytes was detected by using a heterologous mixed lymphocyte (MLR) reaction. The effect of the present or absence of the anti-PD-1 human monoclonal antibody on IFN-γ secretion by T cells was determined. Human CD4+ T cells were obtained by purifying from PBMC with a CD4+ negative selection kit (Miltenyi Biotech). Dendritic cells were derived from the purified monocytes which were cultured with 1000 U/ml IL-4 and 500 U/ml GM-CSF (R&D Biosystems) for seven days. Each MLR reaction involves $10^5$ purified T cells and $10^4$ allogeneic dendritic cells in a total volume of 200 μl. The humanized anti-PD-1 monoclonal antibody was added into a culture plate with different concentrations, after culturing the cells at 37° C. for 5 days, 100 μl culture supernatant was taken to measure the cytokine contents. The measurement of IL-2 was performed by the same method as in Example 7, with the result as shown in FIG. 5 Anti-PD-1 BA08-1 and BA08-2 antibodies significantly promoted T cell activation, and increase IL-2 expression in a dose-dependent manner, with the effects being significantly superior to that of MK-3475.

Figure 6:
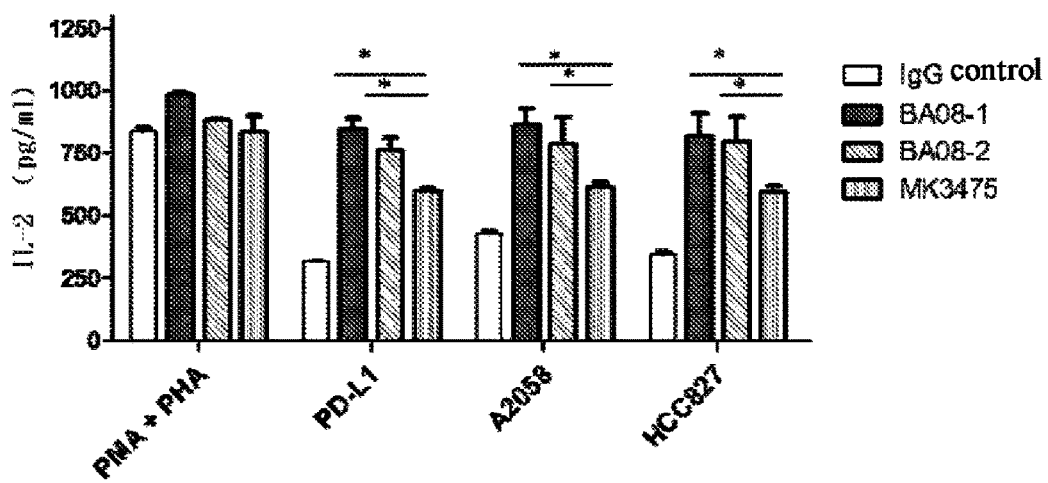
FIG. 6 shows the effects of antibodies BA08-1 and BA-08-2 on tumor cells (including melanoma cell and lung cancer cell) to inhibit IL-2 production of activated T cells, wherein PD-L1 is immobilized PD-L1.

Example 9. Effect of Anti-PD-1 Antibody on Tumor Cell's Inhibition of IL-2 Production of Activated T Cell The cells from human melanoma cell line A2058 and human lung cancer cell line HCC827 were purchased from ATCC (Manassas, Va.). Recombinant human interferon (IFN)-γ, phorbol 12-myristate 13-acetate (PMA) and phytohemagglutinin (PHA) were purchased from Sigma-Aldrich (St. Louis, Mo.). The melanoma and lung cancer cells were grown in complete RPMI 1640 medium to 80% confluence, then 500 U/mL recombinant human IFN-γ was added for treatment for more than 48 hours to up-regulate PD-L1 expression, which was confirmed by a flow cytometer with a mouse anti-human PD-L1 antibody (BD Pharmingen, Cat #557924). Peripheral blood T cells of resting human were obtained by a negative selection through CD3+ T cell enriching column (R&D Systems). The resulting T cells were treated with 1 μg/mL PHA and 50 ng/mL PMA overnight, then added into a 96-well plate precoated with 1 μg/ml recombinant PD-L1-Fc protein (Corning, N.Y.) (marked as PD-L1 in FIG. 6); or in the presence of 3 μg/ml the antibody (IgG control, anti-PD-1 antibody BA08-2 or BA08-1 of the present invention, or MK3475), added to IFN-γ treated tumor cells in a ratio of 6:1 (tumor cells: T cells) and incubated for 48 hrs (marked as A2058 and HCC827 in FIG. 6); or without any further treatment (control, marked as PMA+PHA in FIG. 6). The supernatant was collected and detected for IL-2 expression by ELISA. As shown in FIG. 6, the immobilized PD-L1 can inhibit the IL-2 producing ability of the activated T cells, and anti-PD-1 BA08-1 and BA08-2 antibodies significantly eliminate the inhibitory effect of PD-L1. Similarly, IFN-γ pretreated tumor cells also exhibit inhibition of the IL-2 expression mediated by activated T-cells, and the inhibitory effect can also be blocked by anti-PD-1 BA08-1 and BA08-2 antibodies (*$p<0.05$), and the effect of the antibody of the present invention is significantly better than that of MK-3475.

Figure 7:
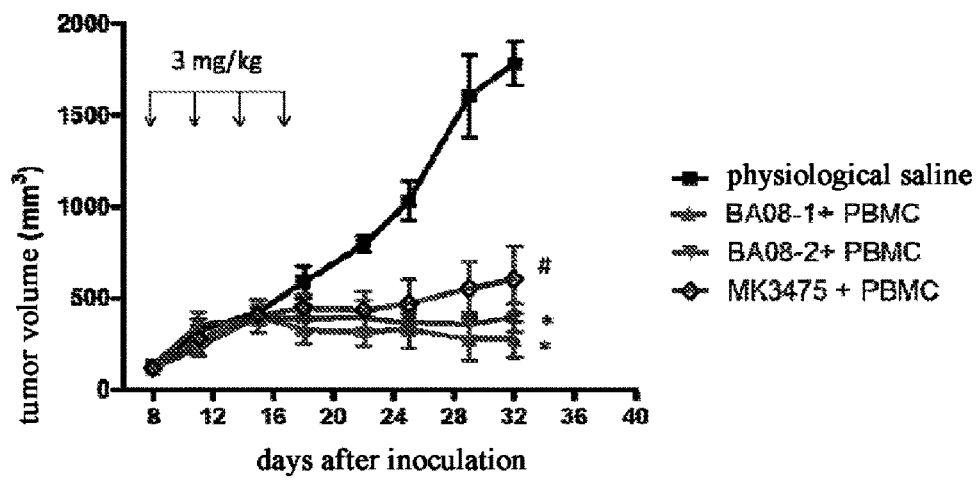
FIG. 7 shows the evaluation of in vivo anti-tumor effect of the humanized anti-PD-1 antibody using Hu-PBL SCID mice having human lung cancer.

Example 10. In Vivo Experiment of Anti-PD-1 Antibody of the Present Invention for Treatment of Lung Cancer To evaluate the in vivo effect of the humanized anti-PD-1 antibody, at Day 1 of the experiment, NOD-SCID mice of 6-week-old were subcutaneously inoculated with $1\times10^7$ HCC827 human lung cancer cells obtained from tissue culture. The treatment is started at Day 8 when the average tumor volume reaches 100 mm$^3$ (55-150 mm$^3$), with 6 animals in each group, and all animals were intraperitoneally injected with the human PBMC in the same batch. The preparation method for the human PBMC is as described above. The PBMC is obtained by Ficoll purification method within 3 hours. Each mouse was inoculated by intraperitoneal injection with a RPMI suspension containing $1\times10^7$ human PBMC and intraperitoneally injected with the antibody on the same day, twice a week at a dose of 5 mg/kg, totaling four doses. The mouse tumor volume was measured twice a week with a caliper, and was calculated using the following formula: Volume=(length×width$^2$)/2. As shown in FIG. 7, the humanized anti-PD-1 antibody showed the effective and long-lasting anti-tumor activity, and the effect of the antibody of the present invention was significantly better than that of MK-3475. Compared to the control group, the tumor inhibition rates of anti-PD-1 BA08-1 and BA08-2 antibodies at Day 32 were 84.5% and 77.8% ($p<0.01$) respectively, which were significantly increased than MK3475 sample with a tumor inhibition rate of 66% ($p<0.05$).

Figure 8:
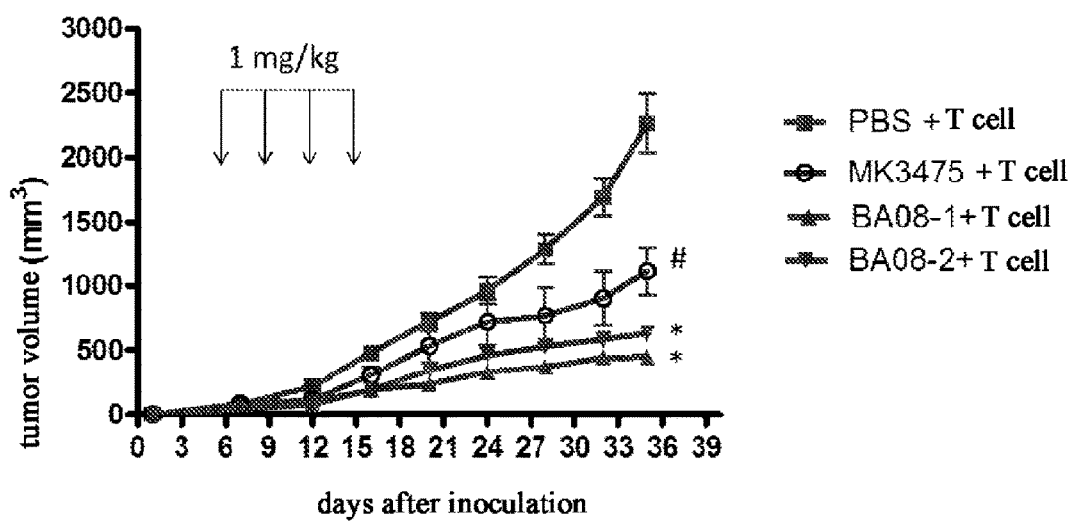
FIG. 8 shows the evaluation of in vivo anti-tumor effect of the humanized anti-PD-1 antibody against melanoma.

Example 11. In Vivo Experiment of Anti-PD-1 Antibody of the Present Invention for Treatment of Melanoma NOD-SCID mice of 6-week-old were subcutaneously inoculated with both $2\times10^6$ A375 human melanoma cells and $1\times10^6$ human T cells stimulated by the same tumor cells which were obtained from tissue culture. The human T cells stimulated by the tumor cells were obtained as follows: negatively selected T cells from the peripheral blood mononuclear cells in healthy human by RosetteSep kit (Stemcell technologies) were co-cultured with A375 human melanoma cells treated with 2 μg mitomycin C for 16 hours in 10% FBS-RPMI culture medium containing 50 U/ml recombinant IL-2 for seven days, and collected for use. The treatment was started on the same day with 6 animals included in each group, and the animals were intraperitoneally injected with the anti-PD-1 antibody twice a week with a dose of 3 mg/kg, with a total of four doses. The mouse tumor volume was measured twice a week with a caliper, and was calculated using the following formula: Volume=(length×width$^2$)/2. As shown in FIG. 8, compared to the control group, the tumor inhibition rates of anti-PD-1 BA08-1 and BA08-2 antibodies at Day 35 were 82% and 72% ($p<0.01$) respectively, which were significantly increased than MK3475 sample with a tumor inhibition rate of 58% ($p<0.05$).

The above preferred embodiments are described only by way of example and not as limitations for a combination of the essential features for carrying out the present invention. The titles provided are not intended to limit the various embodiments of the present invention. The terms such as "comprise", "contain" and "include" are not intended to be limitations. In addition, unless otherwise indicated, when a noun is not modified by a numeral, it includes its plural form, and "or" means "and/or". Unless otherwise indicated, all technical and scientific terms used herein have the same meaning as commonly understood by those skilled in the art.

All publications and patents mentioned in this application are incorporated herein by reference. Without departing from the scope and spirit of the present invention, the various modifications and variations of the methods and compositions described in the present invention are apparent to those skilled in the art. While the present invention is described by way of the specific and preferred embodiments, it will be understood that the invention as claimed should not be improperly limited to such specific embodiments. In fact, many variants apparent to those skilled in the art for carrying out the described modes of the present invention are intended to be included within the scope of the appended claims.

The invention claimed is:

1. An antibody comprising a heavy chain and a light chain, which is capable of specifically binding to PD-1, wherein
the heavy chain comprises a heavy chain variable region which has the amino acid sequence represented by SEQ ID NO: 1, and the light chain comprises a light chain variable region which has the amino acid sequence represented by SEQ ID NO: 3; or
the heavy chain comprises a heavy chain variable region which has the amino acid sequence represented by SEQ ID NO: 4, and the light chain comprises a light chain variable region which has the amino acid sequence represented by SEQ ID NO: 6.

2. The antibody according to claim 1, wherein
the heavy chain comprises a heavy chain variable region which has the amino sequence represented by SEQ ID NO: 4, and the light chain comprises a light chain variable region which has the amino sequence represented by SEQ ID NO: 6; and
wherein the antibody further comprises a human IgG4 or IgG1 heavy chain constant region and a human κ light chain constant region.

3. A pharmaceutical composition, which comprises the antibody according to claim 1, and a pharmaceutically acceptable carrier.

4. A pharmaceutical composition, which comprises the antibody according to claim 2, and a pharmaceutically acceptable carrier.

* * * * *

SEQUENCE LISTING

```
<160> NUMBER OF SEQ ID NOS: 17

<210> SEQ ID NO 1
<211> LENGTH: 120
<212> TYPE: PRT
<213> ORGANISM: Mus musculus

<400> SEQUENCE: 1

Glu Val Gln Leu Gln Gln Ser Gly Pro Val Leu Val Lys Pro Gly Ala
1               5                   10                  15

Ser Val Lys Met Ser Cys Lys Ala Ser Gly Tyr Thr Phe Thr Ser Tyr
            20                  25                  30

Tyr Met Tyr Trp Val Lys Gln Ser His Gly Lys Ser Leu Glu Trp Ile
        35                  40                  45
```

-continued

Gly Gly Val Asn Pro Ser Asn Gly Gly Thr Asn Phe Asn Glu Lys Phe
        50                  55                  60

Lys Ser Lys Ala Thr Leu Thr Val Asp Lys Ser Ser Ser Thr Ala Tyr
 65                 70                  75                  80

Met Glu Leu Asn Ser Leu Thr Ser Glu Asp Ser Ala Val Tyr Tyr Cys
                85                  90                  95

Ala Arg Arg Asp Tyr Arg Tyr Asp Met Gly Phe Asp Tyr Trp Gly Gln
                100                 105                 110

Gly Thr Thr Leu Thr Val Ser Ser
            115             120

<210> SEQ ID NO 2
<211> LENGTH: 120
<212> TYPE: PRT
<213> ORGANISM: Mus musculus

<400> SEQUENCE: 2

Glu Val Gln Leu Gln Gln Ser Gly Pro Glu Leu Val Lys Pro Gly Ala
 1               5                   10                  15

Ser Val Lys Ile Ser Cys Lys Ala Ser Gly Tyr Thr Phe Thr Asn Tyr
                20                  25                  30

Tyr Met Tyr Trp Val Lys Gln Ser His Gly Lys Ser Leu Glu Trp Ile
            35                  40                  45

Gly Gly Ile Asn Pro Ser Asn Gly Gly Thr Asn Tyr Asn Glu Lys Phe
        50                  55                  60

Lys Asn Lys Ala Thr Leu Thr Val Asp Lys Ser Ser Ser Thr Ala Tyr
 65                 70                  75                  80

Met Glu Leu Asn Ser Leu Thr Ser Glu Asp Ser Ala Val Tyr Tyr Cys
                85                  90                  95

Ala Arg Arg Asp Tyr Arg Tyr Asp Met Gly Phe Asp Tyr Trp Gly Ala
                100                 105                 110

Gly Thr Thr Val Thr Val Ser Ser
            115             120

<210> SEQ ID NO 3
<211> LENGTH: 111
<212> TYPE: PRT
<213> ORGANISM: Mus musculus

<400> SEQUENCE: 3

Gln Ile Val Leu Thr Gln Ser Pro Ala Ile Met Ser Ala Ser Pro Gly
 1               5                   10                  15

Glu Lys Val Thr Met Thr Cys Arg Ala Ser Lys Gly Val Ser Thr Ser
                20                  25                  30

Gly Tyr Ser Tyr Leu His Trp Tyr Gln Gln Lys Pro Gly Ser Ser Pro
            35                  40                  45

Arg Leu Leu Ile Tyr Leu Ala Ser Tyr Leu Glu Ser Gly Val Pro Val
        50                  55                  60

Arg Phe Ser Gly Ser Gly Ser Gly Thr Ser Tyr Ser Leu Thr Ile Ser
 65                 70                  75                  80

Arg Met Glu Ala Glu Asp Ala Ala Thr Tyr Tyr Cys Gln His Ser Arg
                85                  90                  95

Glu Leu Pro Leu Thr Phe Gly Thr Gly Thr Arg Leu Glu Ile Lys
                100                 105                 110

<210> SEQ ID NO 4
<211> LENGTH: 120

```
<212> TYPE: PRT
<213> ORGANISM: Artificial Sequence
<220> FEATURE:
<223> OTHER INFORMATION: Synthesized heavy chain variable region of
      humanized antibody BA08-1 for 10F8

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Gly Val Asn Pro Ser Asn Gly Gly Thr Asn Phe Asn Glu Lys Phe
    50                  55                  60

Lys Ser Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Tyr Arg Tyr Asp Met Gly Phe Asp Tyr Trp Gly Gln
            100                 105                 110

Gly Thr Thr Val Thr Val Ser Ser
        115                 120

<210> SEQ ID NO 5
<211> LENGTH: 120
<212> TYPE: PRT
<213> ORGANISM: Artificial Sequence
<220> FEATURE:
<223> OTHER INFORMATION: Synthesized heavy chain variable region of
      humanized antibody BA08-2 for 15H6

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Lys Gln Ala Pro Gly Gln Gly Leu Glu Trp Ile
        35                  40                  45

Gly Gly Ile Asn Pro Ser Asn Gly Gly Thr Asn Tyr Asn Glu Lys Phe
    50                  55                  60

Lys Asn Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Arg Asp Tyr Arg Tyr Asp Met Gly Phe Asp Tyr Trp Gly Gln
            100                 105                 110

Gly Thr Thr Val Thr Val Ser Ser
        115                 120

<210> SEQ ID NO 6
<211> LENGTH: 111
<212> TYPE: PRT
<213> ORGANISM: Artificial Sequence
<220> FEATURE:
<223> OTHER INFORMATION: Synthesized light chain variable region of
      humanized antibody BA08-1 and BA08-2 for 10F8 and 15H6

<400> SEQUENCE: 6

Glu Ile Val Leu Thr Gln Ser Pro Ala Thr Leu Ser Leu Ser Pro Gly
```

```
            1               5                  10                 15
         Glu Arg Ala Thr Ile Ser Cys Arg Ala Ser Lys Gly Val Ser Thr Ser
                        20                  25                 30

Gly Tyr Ser Tyr Leu His Trp Tyr Gln Gln Lys Pro Gly Gln Ala Pro
                    35                  40                  45

Arg Leu Leu Ile Tyr Leu Ala Ser Tyr Leu Glu Ser Gly Val Pro Ala
                50                  55                  60

Arg Phe Ser Gly Ser Gly Ser Gly Thr Asp Phe Thr Leu Thr Ile Ser
         65                  70                  75                  80

Ser Leu Glu Pro Glu Asp Phe Ala Thr Tyr Tyr Cys Gln His Ser Arg
                        85                  90                  95

Glu Leu Pro Leu Thr Phe Gly Thr Gly Thr Lys Val Glu Ile Lys
                        100                 105                 110
```

```
<210> SEQ ID NO 7
<211> LENGTH: 10
<212> TYPE: PRT
<213> ORGANISM: Mus musculus

<400> SEQUENCE: 7

Gly Tyr Thr Phe Thr Ser Tyr Tyr Met Tyr
1               5                   10

<210> SEQ ID NO 8
<211> LENGTH: 17
<212> TYPE: PRT
<213> ORGANISM: Mus musculus

<400> SEQUENCE: 8

Gly Val Asn Pro Ser Asn Gly Gly Thr Asn Phe Asn Glu Lys Phe Lys
1               5                   10                  15
Ser

<210> SEQ ID NO 9
<211> LENGTH: 10
<212> TYPE: PRT
<213> ORGANISM: Mus musculus

<400> SEQUENCE: 9

Gly Tyr Thr Phe Thr Asn Tyr Tyr Met Tyr
1               5                   10

<210> SEQ ID NO 10
<211> LENGTH: 17
<212> TYPE: PRT
<213> ORGANISM: Mus musculus

<400> SEQUENCE: 10

Gly Ile Asn Pro Ser Asn Gly Gly Thr Asn Tyr Asn Glu Lys Phe Lys
1               5                   10                  15
Asn

<210> SEQ ID NO 11
<211> LENGTH: 11
<212> TYPE: PRT
<213> ORGANISM: Mus musculus

<400> SEQUENCE: 11

Arg Asp Tyr Arg Tyr Asp Met Gly Phe Asp Tyr
1               5                   10
```

```
<210> SEQ ID NO 12
<211> LENGTH: 15
<212> TYPE: PRT
<213> ORGANISM: Mus musculus

<400> SEQUENCE: 12

Arg Ala Ser Lys Gly Val Ser Thr Ser Gly Tyr Ser Tyr Leu His
1               5                   10                  15

<210> SEQ ID NO 13
<211> LENGTH: 6
<212> TYPE: PRT
<213> ORGANISM: Mus musculus

<400> SEQUENCE: 13

Leu Ala Ser Tyr Leu Glu
1               5

<210> SEQ ID NO 14
<211> LENGTH: 9
<212> TYPE: PRT
<213> ORGANISM: Mus musculus

<400> SEQUENCE: 14

Gln His Ser Arg Glu Leu Pro Leu Thr
1               5

<210> SEQ ID NO 15
<211> LENGTH: 360
<212> TYPE: DNA
<213> ORGANISM: Artificial Sequence
<220> FEATURE:
<223> OTHER INFORMATION: Synthesized heavy chain variable region of
      the humanized anti-PD-1 antibody for BA08-1

<400> SEQUENCE: 15
caggtccagc tcgtgcaatc cggagccgaa gtgaaaaagc ctggcgcttc cgtcaaggtc    60
tcctgtaagg cttccggata cacattcaca tcctattaca tgtattgggt caggcaagcc   120
cctggccaag cctcgagtg atgggaggc gtcaacccctt ccaatggcgg aaccaatttc    180
aatgagaaat tcaaatcccg ggtgacaatc acagccgata agagcaccag caccgcttac   240
atggaactga gctccctcag gagcgaggat accgctgtgt attactgtgc ccggagggat   300
taccggtacg atatgggatt cgattactgg ggacagggaa ccacagtgac agtgagctcc   360

<210> SEQ ID NO 16
<211> LENGTH: 360
<212> TYPE: DNA
<213> ORGANISM: Artificial Sequence
<220> FEATURE:
<223> OTHER INFORMATION: Synthesized heavy chain variable region of
      the humanized anti-PD-1 antibody for BA08-2

<400> SEQUENCE: 16
caggtccagc tcgtgcaatc cggagccgaa gtgaaaaagc ctggcgcttc cgtcaaggtc    60
tcctgtaagg cttccggata cacattcaca aactattaca tgtattgggt caagcaagcc   120
cctggccaag cctcgagtg attggcgga atcaatccca gcaacggagg cacaaactat    180
aacgaaaagt ttaagaataa ggctacccctc accgctgaca atccacatc cacagcctat   240 atggaactga gctccctcag gagcgaggat accgctgtgt attactgtac ccggagggat   300
taccggtacg atatgggatt cgattactgg ggacagggaa ccacagtgac agtgagctcc   360
```

<210> SEQ ID NO 17
<211> LENGTH: 333
<212> TYPE: DNA
<213> ORGANISM: Artificial Sequence
<220> FEATURE:
<223> OTHER INFORMATION: Synthesized light chain variable region of
      the humanized anti-PD-1 antibody

<400> SEQUENCE: 17

```
gagattgtgc tcacccaatc ccctgccaca ctgagcctga gccccggaga gcgggccaca      60
atcagctgcc gggccagcaa gggagtgagc accagcggct attcctatct gcattggtat     120
cagcaaaagc ctggccaagc ccctaggctc ctgatttacc tcgccagcta cctcgagagc     180
ggcgtccccg ctaggttttc cggatccgga tccggaaccg atttcacact gacaatcagc     240
tccctcgagc ctgaggattt cgctacctat tactgtcagc attcccggga gctccccctc     300
acctttggca caggcacaaa ggtcgagatt aag                                  333
```